US009964400B1

(12) United States Patent
Jones

(10) Patent No.: US 9,964,400 B1
(45) Date of Patent: May 8, 2018

(54) HEIGHT MEASURING DEVICE

(71) Applicant: Mark Conrad Jones, Austin, TX (US)

(72) Inventor: Mark Conrad Jones, Austin, TX (US)

(*) Notice: Subject to any disclaimer, the term of this patent is extended or adjusted under 35 U.S.C. 154(b) by 0 days. days.

(21) Appl. No.: 15/488,468

(22) Filed: Apr. 15, 2017

Related U.S. Application Data

(62) Division of application No. 15/019,905, filed on Feb. 9, 2016, now Pat. No. 9,658,333.

(51) Int. Cl.
  *G01P 3/36* (2006.01)
  *G01B 11/14* (2006.01)
  *G01B 5/06* (2006.01)

(52) U.S. Cl.
  CPC .............. *G01B 11/14* (2013.01); *G01B 5/061* (2013.01)

(58) Field of Classification Search
  CPC . G01S 17/02; G01S 7/497; G01S 7/51; G01C 9/24; G01B 11/14; G01B 5/061
  See application file for complete search history.

(56) References Cited

U.S. PATENT DOCUMENTS

| | | | | |
|---|---|---|---|---|
| 5,813,132 A | * | 9/1998 | Bodkin, Sr. ............ | G01B 5/061 33/494 |
| 2005/0128465 A1 | * | 6/2005 | Skultety-Betz .......... | G01C 3/08 356/4.01 |
| 2006/0265896 A1 | * | 11/2006 | Kavana ................ | A61B 5/1072 33/832 |
| 2015/0219432 A1 | * | 8/2015 | Liu ........................ | G01B 5/061 33/512 |

* cited by examiner

*Primary Examiner* — Samantha K Abraham

(57) ABSTRACT

An apparatus, method, and system for height-measurement are provided. The apparatus, and method includes initiating, and calibrating a height-measuring-device to capture and store a one-time calibration-mode distance. Then, in operation-mode, a foot-platform connected to a retractable-tape is pulled atop an object/user. Electronic signals from a laser-device are generated as a means to measure both calibration-mode and operation-mode distances. These distances are then resolved and stored as a height-measurement for a user/object, and the resulting height-measurement is displayed on a screen.
The height-measurement data from each object/user are compared to one another. The height-measuring-device also includes a predictive algorithm that determines the future height of users.

10 Claims, 6 Drawing Sheets

FIG. 1    Height Measuring Device

FIG. 2 Height Measuring Device

FIG. 4  Height Measuring Device
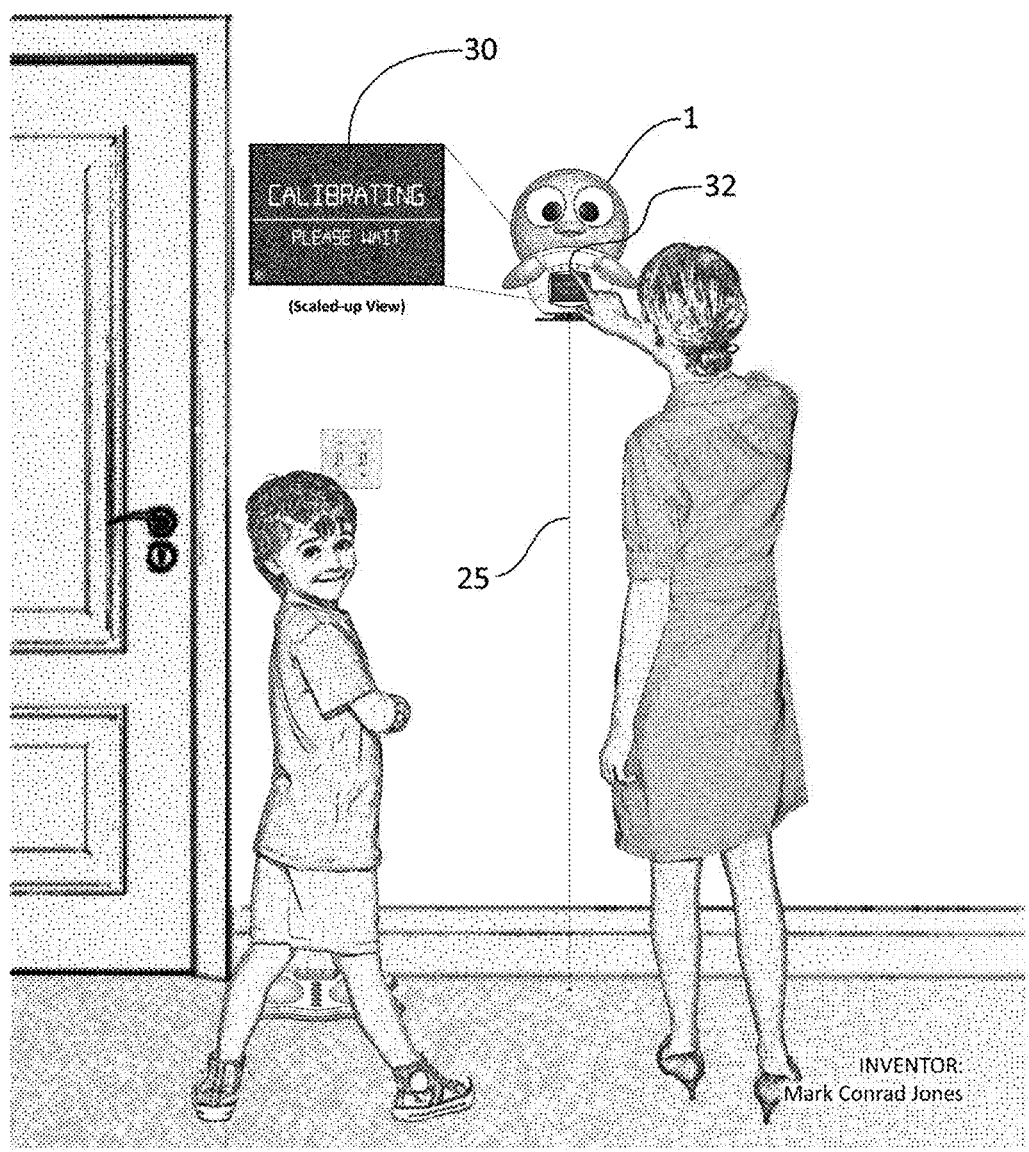

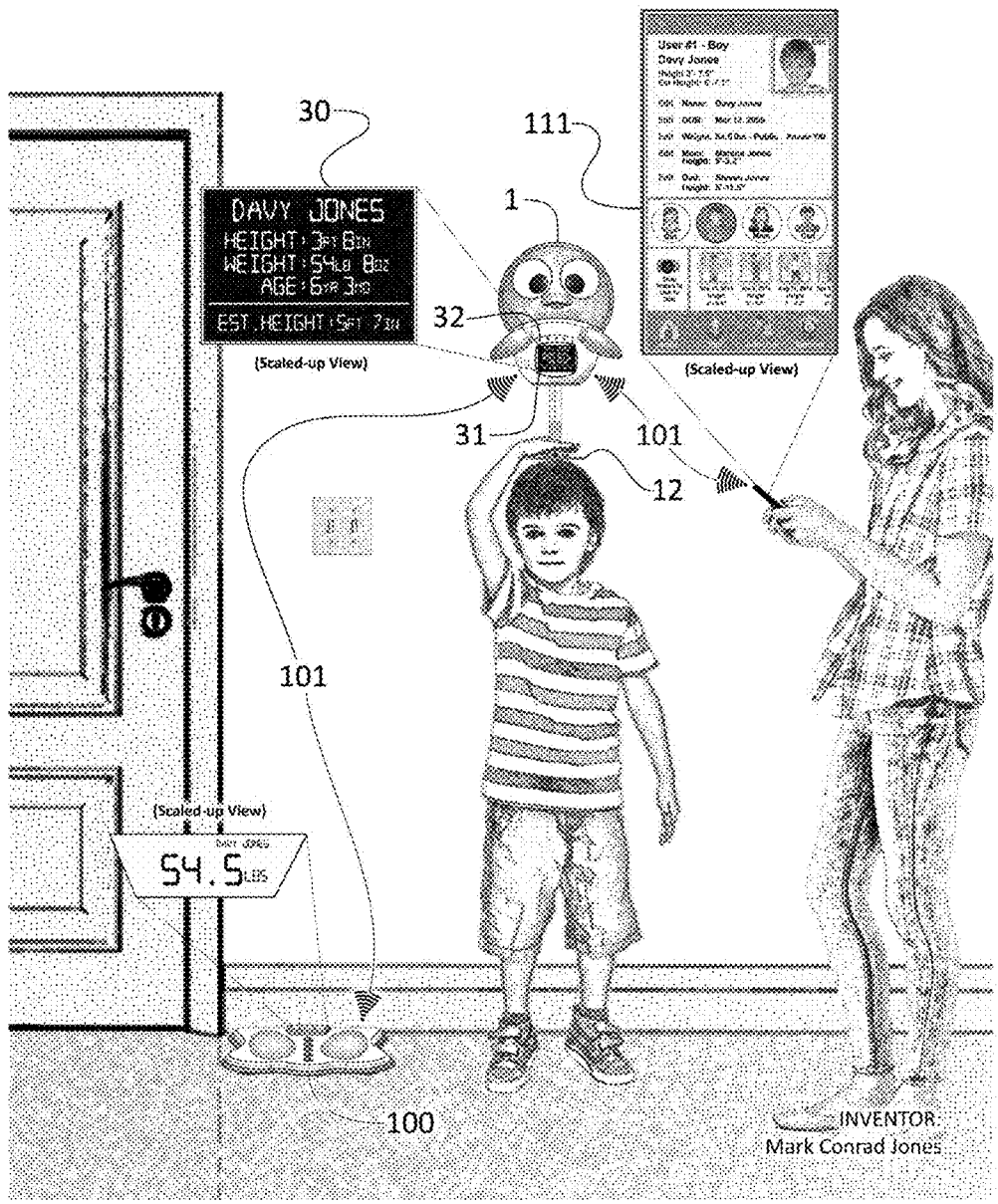
FIG. 5 Height Measuring Device

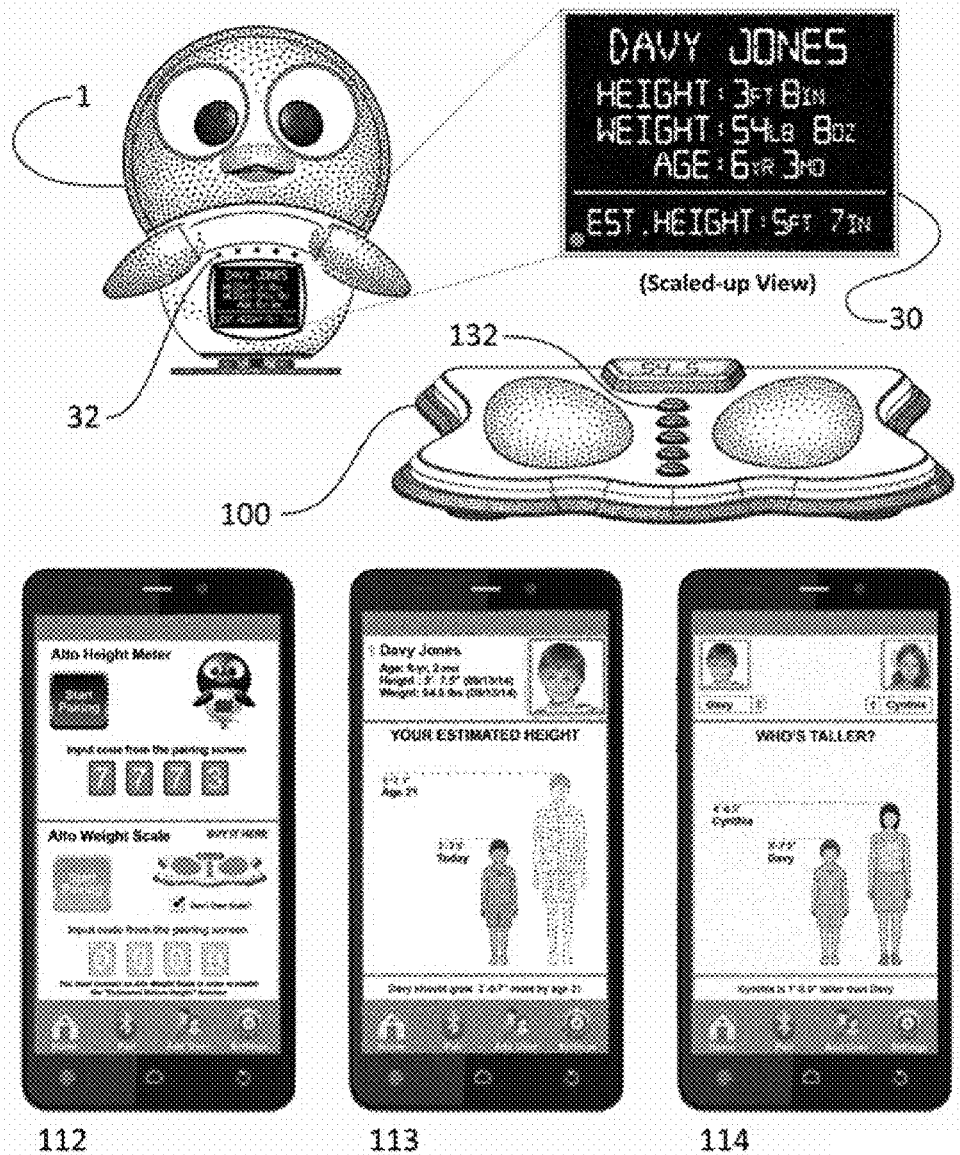

HEIGHT MEASURING DEVICE

BRIEF SUMMARY

An apparatus, method, and system for height-measurement are provided. The apparatus, and method includes initiating, and calibrating a height-measuring-device to capture and store a one-time calibration-mode distance. Then, in operation-mode, a foot-platform connected to a retractable-tape is pulled atop an object/user. Electronic signals from a laser-device are generated as a means to measure both calibration-mode and operation-mode distances. These distances are then resolved and stored as a height-measurement for a user/object, and the resulting height-measurement is displayed on a screen.

The system includes processor instructions that captures, calculates, and stores a calibration-mode distance as well as the calculated height-measurement for one or more objects/users. It then displays calculated height-measurement of the objects/users. Further, height-measurements are compared for more than one object/user. The height-measurement data is processed using a predictive algorithm in order to predict future heights of users. The height-measurement data, including compared heights, and predicted heights are stored, and displayed on a plurality of screens, including smart-phones, scales, tablets, and the like.

This summary is provided to introduce a selection of concepts in a simplified form that are further described in the detailed description. This summary is not intended to identify key features or essential features of the claimed subject matter, nor is it intended to be used to limit the scope of the claimed subject matter.

BACKGROUND OF INVENTION

Field of the Disclosure

The height-measuring-device relates to an apparatus, method, and system for height-measurement.

Background of the Disclosure

Height-measuring-devices have evolved over the years. Traditionally, a person's height is either taken with a limp tape measure at home or at the doctor's office using a bulky, oversized height scale, typically having a floor base. Other wall mounted devices use a long cumbersome graduated rod having a sliding plank, or a basic graduated retractable-tape having a hard to read parallax sight, and a plank.

Several additional electronic height-measuring-devices have been introduced over the past decades to capture height-measurements. Some devices electronically track the vertical position of a person and report the corresponding height-measurement, by physically placing a device on top of a person's head, calculating the person's height by measuring the distance from the floor to the ceiling, and then subtracting the distance from the person's head to the ceiling. However, this requires a clear line of sight to a non-vaulted ceiling, and a floor. Due to the ability of the device sliding off the person's head, it has a higher probability of improperly calculating the person's height.

However, the wall mounted height-measuring-device presented herein provides obvious efficiencies such as not requiring balancing atop of a user's head; nor does it need to be mounted at a prescribed distance from the floor; nor does it require on a cumbersome door edge mount with multiple setups; nor does it require a bulky floor base apparatus having a long measuring stem; nor is there the issue of parallax error in the reading of its measurement output. The height-measuring-device also provides high resolution and a high level of accuracy through the incorporation of a laser distance sensor that calculates heights via the difference of a calibration-mode distance from an operation-mode distance. The wall mounted height-measuring-device is easy to initiate and use as the foot-platform is effortlessly conveyed atop of an object/user in order to both activate and capture a height-measurement. Last, the height-measuring-device provides for a safe barrier between human eyes and the UV laser-beam via the foot-platform which blocks the beam, making this height-measuring-device eye-safe.

DETAILED DESCRIPTION

FIG. 1 depicts a height-measuring-device [1] comprising a housing having a front-shell-assembly [9] and corresponding rear-facing-shell [50]. The front-shell-assembly [9] in a decorative embodiment includes a head [2] having a molded snap tab [7], a belly [5] having a display-aperture [10], a screen-display [30] having an integrated camera [31], at least one pushbutton [32], and decorative-arms [3]. However, the front-shell-assembly [9] is not limited to having decorative facade features and is purely functional in design. The foot-platform [12], having a slider-tab [24] shown in a closed position, perpendicularly abuts the underside of the belly [5] and the bottom of the rear-facing-shell [50] of the housing. The foot-platform [12] includes at least one bumper [20] to prevent the foot-platform [12] from directly contacting and damaging the underside of the housing. The foot-platform [12] shown in drawings includes a decorative design, such as molded toe cutouts to heighten user experience.

FIG. 2. depicts the height-measuring-device [1] with the foot-platform [12] in a partially extended position. The foot-platform [12] is connected to a retractable-tape [15] and is affixed by a foot-bracket [23] or other attachment. The retractable-tape [15] has similar form and structure to that of a spring-loaded tape measure. In this view, a laser-beam [25] projects in a vertical downward manner from the underside of the shell-assembly [9] towards the foot-platform [12], namely onto the slider-tab [24] being in a closed position.

FIG. 3 is an exploded view of the height-measuring-device [1], wherein a time-of-flight type laser-device [37] is fixed onto a sensor-bracket [42]. The laser-device [37] captures height-measurements of users/objects by means of a laser-beam [25] reflecting off of the slider-tab [24] in its closed position, which is located on the topside of the retractable foot-platform [12]. The foot-platform [12] has an aperture [61] positioned and hidden underneath the slider-tab [24], and the slider-tab [24] is closed during operation mode of the height-measuring-device. Otherwise, the aperture [61] is exposed when the slider-tab [24] is pulled away from the aperture [61], and is in its open position during calibration-mode of the height-measuring-device [1]. The retractable-tape [15] is made from thin, rigid, but flexible material, and is contained within a spring loaded tape-housing [40]. In order to hold the tape-housing [40] into place, it is inserted between walls [53], which protrude perpendicularly from the rear-facing-shell [50]. When the foot-platform [12] is pulled down vertically, the retractable-tape [15] synchronously travels downward while the remaining length of the retractable-tape [15] remains in a coiled state within the spring loaded tape-housing [40]. As the retractable-tape [15] extends, it exits from the tape-housing

[40], becoming uncoiled, and passes through a partially surrounding sensor-bracket [42], which keeps the retractable-tape [15] confined within a certain clearance. The retractable-tape [15] and foot-bracket [23] provides vertical parallelism and horizontal rigidity of the foot-platform [12] along its travel path. The rear-facing-shell [50] is configured to be mountable onto a surface, such as a wall, using mounting screws [46] and washers [47]. Bubble type or electronic level-indicator [45] are affixed within the housing onto the interior of the rear-facing-shell [50], to ensure the height-measuring-device [1] has the truest perpendicular wall mount with respect to the floor. The rear-facing-shell [50] attaches to the front-shell-assembly [9] using one or more fasteners [56] through molded bosses [55]. The head [2] section attaches, or detaches, by means of one or more molded-snap-tabs [7], providing for a non-fastener access to the power-supply/battery [60], as well as convenient access to the mounting screws [46] of the height-measuring-device [1] itself.

A screen-display [30] having an integrated camera [31] is incorporated into the front-shell-assembly [9] and is positioned adjacent to a corresponding Application Specific Integrated Circuit (ASIC)-board [35]. The ASIC-board [35] houses system hardware such as pushbuttons [32], processors, wireless radios, memory modules, voice recognition modules, face recognition modules, camera modules, microphones, audio speakers, and other electronics and microelectronics. Along with the pushbuttons [32], the screen-display [30] is used as a touch screen that enables the user to press buttons, add information, and manipulate objects using Graphic User Interface (GUI) buttons on the screen-display [30]. Camera [31] is used for user face recognition and object photographs. The height-measuring-device [1] software accepts user and object inputs information, such as individual, or family member assignment, and can send data to the corresponding LED, LCD or similar screen-display [30]. These options allow the user to easily input, initiate, manipulate, and associate user/object information, and password functionality.

Once the foot-platform [12] is pulled downward and comes to rest atop of a user/object for a certain time, such as 3 seconds, the laser-device [37] fires a downward directed laser-beam [25] from its fixed mounting position on the sensor-bracket [42] and reflects off of the foot-platform's [12] slider-tab [24]. Next, the laser-device's [37] processor and algorithm instantaneously evaluate the time-of-flight data and output the precise travel distance measurement of the plain retractable-tape [15] and the adjoined foot-platform [12]. Technologically, the laser-device [37] heretofore is mentioned as being of the time-of-flight type, but may utilize triangulation, or other technology that supports line-of-sight distance measurement.

FIG. 4 depicts the height-measuring-device [1] in calibration-mode and illustrates the calibration-mode process for the laser-device [37]. After mounting the height-measuring-device [1] onto a wall or other surface, the height-measuring-device [1] should be calibrated electronically in order to record its relative position with respect to the floor or other surface. Referencing FIG. 3, the foot-platform [12] has a slider-tab [24], which perpendicularly extends, and is slidable across the aperture [61] allowing the user to open or close the aperture [61] and thereby selecting either operation-mode or calibration-mode of the height-measuring-device [1]. During calibration-mode, the foot-platform [12] abuts the height-measuring-device [1], and the slider-tab [24] on the foot-platform [12] automatically slides into an open position, or is manually slid open by the user. Once the slider-tab [24] is open, the aperture [61] is exposed, and the laser-beam [25] has a clear line of sight through the foot-platform's aperture [61], to the floor, or other surface. To initiate calibration-mode, a pushbutton [32] is manually depressed for a certain period of time, such as 7 seconds, or the calibration-mode is alternately activated via the touch-screen screen-display [30], or by voice recognition. A concurrent audible beep emits, while the laser-beam [25] instantaneously passes through the aperture [61] and reflects off the floor, or other surface, transmitting the electronic distance signal back to the laser-device [37] processor in order to capture and record the as-mounted calibration-mode distance. The calibration-mode distance is stored in the ASIC-board's [35] memory and is displayed on the screen-display [30], and status information is played from an audio speaker. Once the height-measuring-device [1] is calibrated, the aperture [61] is either manually or automatically re-closed, and the height-measuring-device [1] is now ready for use by users/objects whose physical height is comfortably less than the calibrated as-mounted distance. No separate individualized calibration is necessary, but the height-measuring-device [1] is re-calibrated when the vertical mounting position of height-measuring-device [1] changes.

FIG. 5 illustrates the height-measurement process for a user who is positioned underneath the foot-platform [12]. To use the height-measuring-device for the first time, the new user first programs their personal pushbutton [32], which enables the height-measuring-device [1] to recognize who is about to use the device [1]; this action permanently correlates the user with the specific programmed pushbutton [32]. Likewise, the presence of a personalized pushbutton [32] allows future height-measurements to be added to previously stored personal user data, not limited to previous height, weight, age, name, and gender. Alternately, a user could be automatically recognized via the integrated camera [31] using face recognition software capability.

In operation, the user simply depresses his/her personalized pushbutton [32], and within a certain time-frame, such as 10 seconds, the user pulls the foot-platform [12], or it automatically travels downward until it abuts, and rests flatly on the crown of the user's head. Once the foot-platform [12] comes to rest on user's head for a predetermined time, such as 3 seconds, an audible beep emits, and the laser-device [37] will automatically capture, and store in memory, the operation-mode distance of the foot-platform [12]. The total user/object height-measurement calculation is simply the difference between the stored as-mounted calibration-mode distance, and the operation-mode travel distance of the foot-platform [12] as it comes to rest atop its target below. The ASIC-board's system algorithm will cache, log, and save the digital height: and this data will be displayed on the screen-display [30] and played from an audio speaker. Wired or wireless [101] data transmissions from the height-measuring-device [1] are shared with a scale [100], a smart-phone [111], or other connected user device. Here, the height-measuring-device's screen-display [30] is not limited to displaying the user's first and last name, height, weight, age, estimated height, and photograph. Concurrently, the connected smart-phone [111] is not limited to displaying shared data that include the user's first and last name, current height, estimated future height, DOB, weight, gender, privacy settings, mother's name, mother's height, father's name, father's height, as well as user photographs, that are age, date, and height stamped. Similarly, the connected scale [100] is not limited to displaying the user's name, weight, and the like.

FIG. 6 depicts the system, including the height-measuring-device [1] connected to a proprietary weight scale [100] having shared data, memory, and foot-activated pushbuttons [132] corresponding to the height-measuring-device's push-buttons [32]. It also depicts smart-phones [112], [113], and [114] which represent connected possibilities such as tablets, monitors, personal computers, smart-phones, or other devices. Smart-phone [113] illustrates a screen, wherein the height-measuring-device [1] is calculating, and displaying, a scaled graphical representation of a user's height juxtapose to a figure representing his/her comparative future height. This predictive height computation correlates the user's data with his/her family's user data to produce a height prediction. Smart-phone [114] illustrates a screen, wherein the height-measuring-device [1] is calculating, and displaying, a scaled graphical representation of the user's height juxtapose to a comparative figure of a family member of equal, or different height. This height comparison is simply a raw comparison of the user's height data with respect to another user's height data. Smart-phone [112] illustrates a screen in the process of receiving and transmitting pairing codes to the height-measuring-device [1], and to the weight scale [100] respectively. Once connected devices have been paired, and information synced and accumulated, the data outputs will be displayed, shared, printed, and saved. The general scope of the height-measuring-device's [1] data set includes, but is not limited to: personal information, sibling information, parent information, family tree data, medical records, demographic information, and other shared demographic API data.

THE DESCRIPTION OF THE DISCLOSURE HAS BEEN PRESENTED FOR PURPOSES OF ILLUSTRATION AND DESCRIPTION, BUT IS NOT INTENDED TO BE EXHAUSTIVE OR LIMITED IN THE FORM DISCLOSED. IT WILL BE APPARENT TO THOSE OF SKILL IN THE ART THAT MANY MODIFICATIONS AND VARIATIONS ARE POSSIBLE WITHOUT DEPARTING FROM THE SCOPE AND SPIRIT OF THE DISCLOSURE, GIVING FULL COGNIZANCE TO EQUIVALENTS IN ALL RESPECTS.

BRIEF DESCRIPTION OF DRAWINGS

The height-measuring-device is illustrated by the following non-limiting drawings in which:

FIG. 4 is an illustrative view of the height-measuring-device being calibrated using a laser device.

FIG. 5 is an illustrative view of the height-measuring-device showing user engagement.

FIG. 6 is an illustrative view of the height-measuring-device corresponding to a smart-phone application and a scale and showing comparative and predictive heights.

Figure 1:
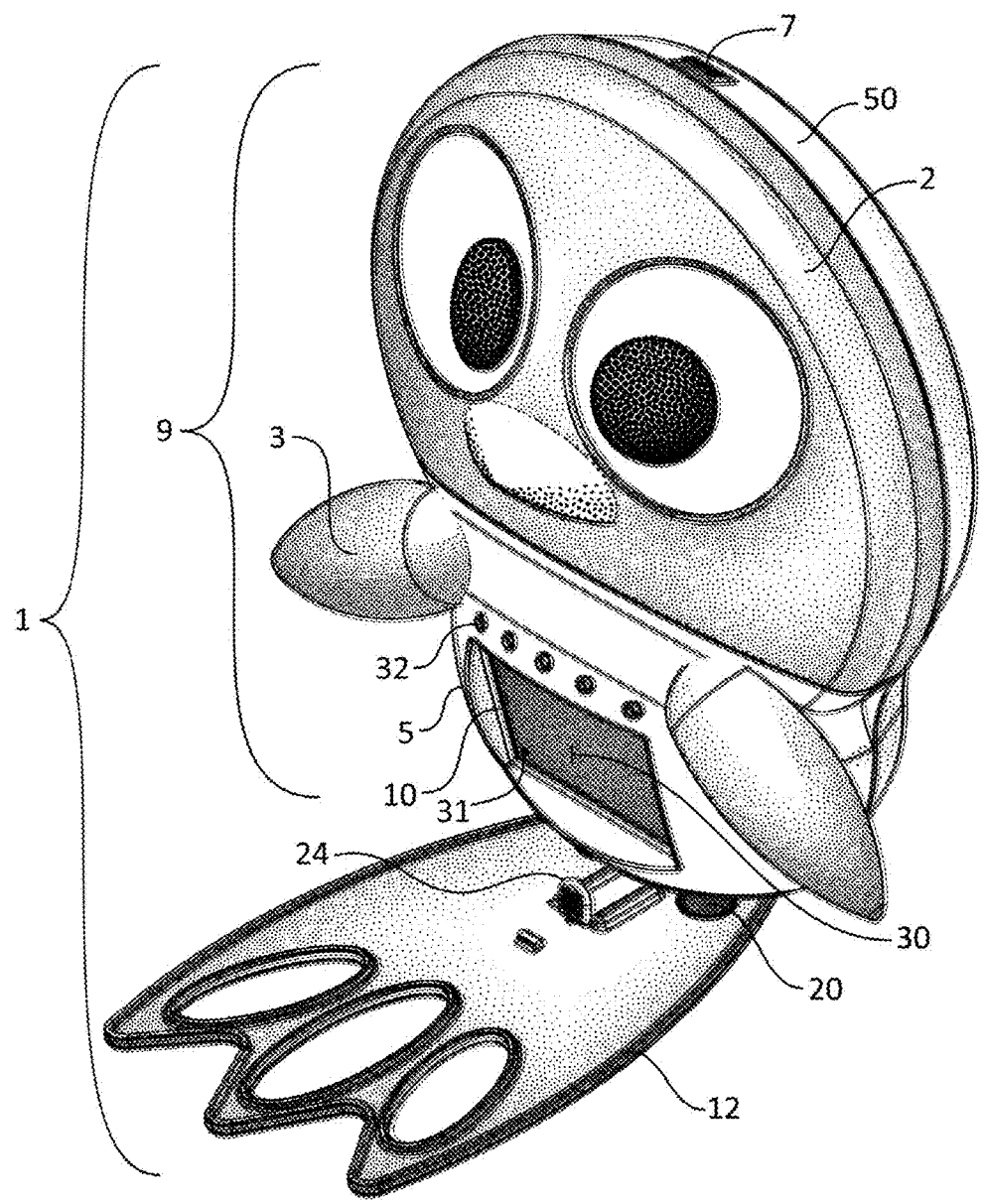
FIG. 1 is a front perspective view of the height-measuring-device.
Figure 2:
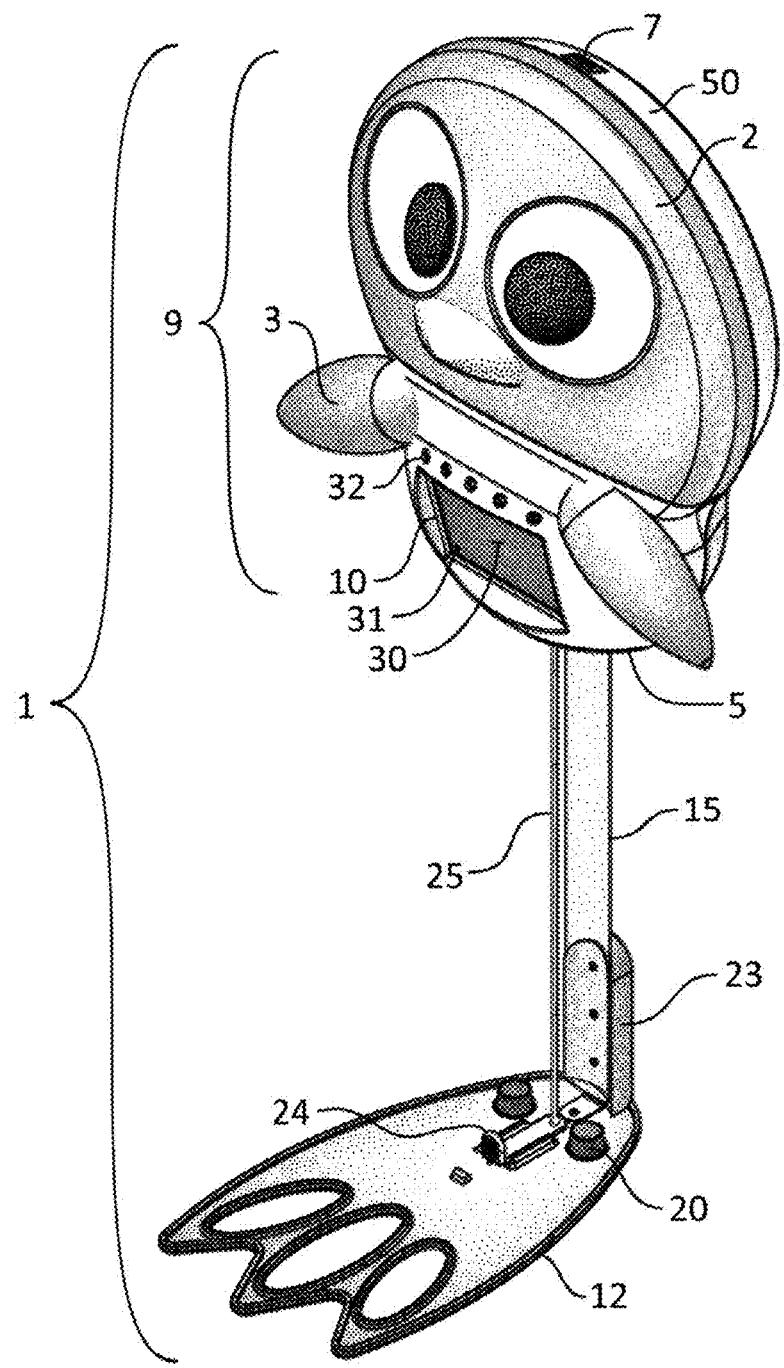
FIG. 2 is an isometric view of the height-measuring-device with the foot in an extended position.
Figure 3:
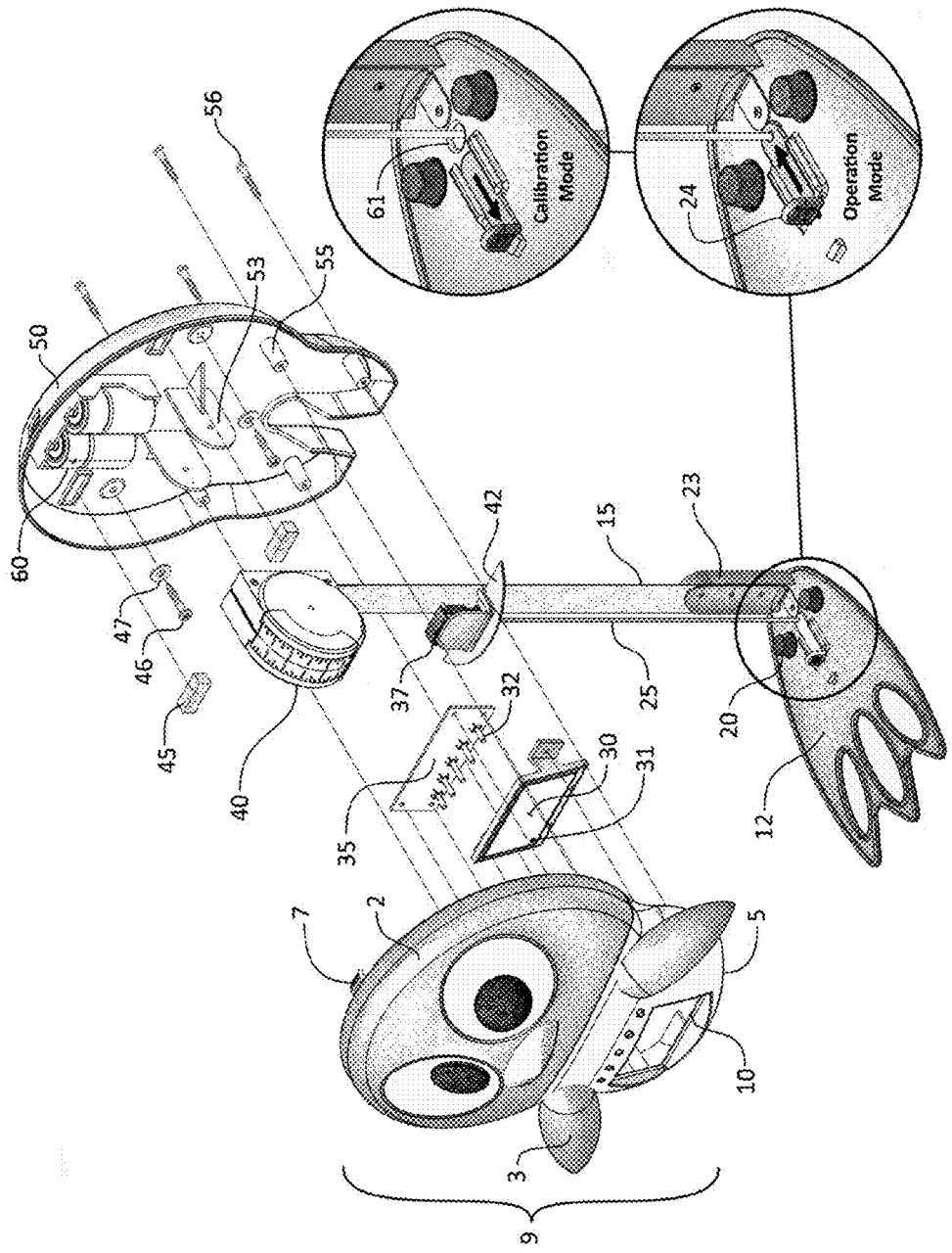
FIG. 3 is an exploded view of the height-measuring-device having a laser device.

The invention claimed is:

1. A method of height-measurement of an user/object, the method comprising:
   permanently mounting a height-measuring-device onto a wall or a surface;
   positioning a slider-tab which covers an aperture on a foot-platform from a first position into a second position that leaves said aperture open and exposed;
   initiating a calibration-mode of said height-measuring-device by triggering a user input such as a pushbutton;
   projecting a laser-beam in a downward direction, away from said mounted height-measuring-device and toward a floor, through said aperture of said foot-platform, wherein said laser-beam reflects perpendicularly off of the floor and then sends this calibration-mode distance back into a laser-device receiver;
   capturing and storing calibration-mode distance in a processor;
   ending said calibration-mode and concurrently readying an operation-mode by positioning said slider-tab into the first position that covers said aperture on said foot-platform;
   initiating the operation mode by activating a user input;
   pulling said foot-platform in a downward direction away from said mounted height-measuring-device, and toward the floor, in order to convey said foot-platform into a rest position atop the user/object to be measured, while holding this resting position for a preset time;
   waiting said preset time, and then projecting said laser-beam in a downward direction away from said mounted height-measuring-device, and toward the floor, and perpendicularly onto a topside of said foot-platform, wherein said laser-beam reflects off of said foot-platform's said slider-tab, while transmitting an operation-mode distance back to said laser-device receiver;
   capturing, and storing said operation-mode distance in processor;
   calculating the user/object's height-measurement by electronically subtracting said operation-mode distance from said calibration-mode distance;
   displaying said height-measurement onto a screen-display;
   selecting a corresponding device to transfer and share said height-measurement; and
   repeating said operation mode to measure a plurality of additional users/objects.

2. The method of claim 1, further comprising mounting said height-measuring-device onto the surface such as an interior wall.

3. The method of claim 1, further comprising transmitting said height-measurement to said corresponding device.

4. The method of claim 1, wherein said corresponding device is selected from the group consisting of a scale, tablet, monitor, personal computer, speaker, and smart-phone.

5. A system for height-measurement of a user/object, the system comprising:
   a processor; and
   a non-transitory computer-readable medium coupled to said processor and storing a plurality of instructions, which when executed, cause said processor to handle height-measurement data, the plurality of instructions comprising:
      instructions that cause said processor to determine that a height-measuring-device has initiated;
      instructions that cause said processor to determine a slider-tab on a foot-platform being in an open position;
      instructions that cause said processor to determine a calibration-mode has initialized;
      instructions that cause said laser beam to be emitted and received at a receiver;
      instructions that cause said processor to determine when a calibration-mode distance is transmitted by a laser-beam reflecting off a surface;

instructions that cause said processor to capture and store said calibration-mode distance;

instructions that cause said processor to determine when said slider-tab on said foot-platform is in a closed position;

instructions that cause said processor to determine when said foot-platform has moved to a downward position atop said user/object;

instructions that cause said laser beam to be emitted and received at said receiver;

instructions that cause said processor to determine when an operation-mode distance is transmitted from said laser-beam reflecting off of said foot-platform's said slider-tab;

instructions that cause said processor to capture and store said operation-mode distance;

instructions that cause said processor to calculate a user/object's height-measurement by subtracting said operation-mode distance from said calibration-mode distance;

instructions that cause said processor to capture and store said user/object's height-measurement; and instructions that cause said processor to send said user/object's height-measurement onto a screen-display.

6. The system of claim 5, further comprising instructions that cause said processor to run an algorithm for predicting the height of said user, the algorithm comprising:

instructions that cause said processor to retrieve stored data of said user; and instructions that cause said processor to retrieve stored data of certain family members of said user; and instructions that cause said processor to utilize said user data, and said stored data of certain family members in order to calculate, and store a predicted height of said user; and instructions that cause the processor to transmit said predicted height of said user onto said screen-display.

7. The system of claim 6, further comprising instructions that cause said processor to run an algorithm predicting the height of a subsequent user and store a predictive height of said subsequent user; and instructions that cause said processor to transmit said predictive height onto said screen-display.

8. The system of claim 7, further comprising instructions that cause said processor to compare predictive heights of at least a pair of users and store said compared predictive heights; and instructions that cause the processor to display said compared predictive heights onto said screen-display.

9. The system of claim 5, further comprising instructions that cause the processor to determine when a subsequent user/object initiates said height-measuring-device, the system comprising:

instructions that cause said processor to determine said height-measuring-device has initiated;

instructions that cause said processor to determine when said foot-platform has moved to a downward position atop said subsequent user/object;

instructions that cause said processor to capture and store downward position as a operation-mode distance;

instructions that cause said processor to calculate a height-measurement of said subsequent user/object by subtracting said operation-mode distance from said calibration-mode distance;

instructions that cause said processor to capture and store the said height-measurement of said subsequent user/object; and instructions that cause said processor to display the said height-measurement of said subsequent user/object onto said screen-display.

10. The system of claim 7, further comprising instructions that cause said processor to compare heights of at least a pair of users/objects and store said compared heights; and instructions that cause said processor to display said compared heights onto said screen-display.

* * * * *